United States Patent
O'Neill et al.

(10) Patent No.: US 10,016,140 B2
(45) Date of Patent: Jul. 10, 2018

(54) AUTOMATED NON-MAGNETIC MEDICAL MONITOR USING SHAPE MEMORY ACTUATORS

(71) Applicant: KONINKLIJKE PHILIPS N.V., Eindhoven (NL)

(72) Inventors: Francis Patrick O'Neill, Kissimmee, FL (US); Ronald Paul Consiglio, Clermont, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 684 days.

(21) Appl. No.: 14/401,708

(22) PCT Filed: Jun. 13, 2013

(86) PCT No.: PCT/IB2013/054828
§ 371 (c)(1),
(2) Date: Nov. 17, 2014

(87) PCT Pub. No.: WO2013/186725
PCT Pub. Date: Dec. 19, 2013

(65) Prior Publication Data
US 2015/0119691 A1 Apr. 30, 2015

Related U.S. Application Data

(60) Provisional application No. 61/658,964, filed on Jun. 13, 2012.

(51) Int. Cl.
*F16K 99/00* (2006.01)
*A61B 5/0235* (2006.01)
(Continued)

(52) U.S. Cl.
CPC .......... *A61B 5/0235* (2013.01); *A61B 5/0225* (2013.01); *A61B 5/02233* (2013.01);
(Continued)

(58) Field of Classification Search
CPC ...... F16K 31/02; F16K 31/002; F16K 31/025; F16K 99/0044; F16K 99/0038; A61B 5/0235; A61B 5/15119
(Continued)

(56) References Cited

U.S. PATENT DOCUMENTS 4,645,489 A * 2/1987 Krumme ........... A61M 5/16813
251/11
5,865,418 A * 2/1999 Nakayama ........... G05D 23/026
251/11
(Continued)

FOREIGN PATENT DOCUMENTS

WO 0159344 A1 8/2001

OTHER PUBLICATIONS

Szczesny, S., et al.; Review of Current Actuator Suitability for Use in Medical Implants; 2006; IEEE Engineering in Medicine and Biology; pp. 5956-5959.

*Primary Examiner* — Matthew W Jellett

(57) ABSTRACT

When employing a valve in a medical device in or near a bore of a magnetic resonance (MR) scanner, MR-compatible materials are employed to minimize the susceptibility of the valve to the strong magnetic fields generated by the MR scanner. An MR-compatible actuator comprises a shame memory alloy (SMA) wire or member (12) that is actuated by application of a constant power signal. The constant power signal is supplied by a control circuit (50) that is generated using a power feedback signal derived from measured current and voltage feedback signals. Once the SMA member is actuated, the power signal can be reduced and pulse width modulated to maintain the SMA member in an active state, which in turn maintains the valve in a closed state until the power signal is terminated.

15 Claims, 4 Drawing Sheets

(51) Int. Cl.
  *F16K 31/00* (2006.01)
  *F16K 31/02* (2006.01)
  *A61B 5/022* (2006.01)
  *A61B 5/0225* (2006.01)
  *A61B 5/151* (2006.01)
  *A61B 17/00* (2006.01)
  *A61M 39/24* (2006.01)

(52) U.S. Cl.
  CPC .......... *F16K 31/002* (2013.01); *F16K 31/025* (2013.01); *F16K 99/0038* (2013.01); *F16K 99/0044* (2013.01); *A61B 5/15119* (2013.01); *A61B 2017/00867* (2013.01); *A61B 2017/00911* (2013.01); *A61M 2039/2486* (2013.01)

(58) Field of Classification Search
  USPC ............................................... 251/11, 129.01
  See application file for complete search history.

(56) References Cited

U.S. PATENT DOCUMENTS

| | | | |
|---|---|---|---|
| 5,984,258 A | 11/1999 | Knebel et al. | |
| 6,019,113 A * | 2/2000 | Allston | F16K 31/025 137/1 |
| 6,114,851 A | 9/2000 | Kruspe et al. | |
| 6,279,869 B1 * | 8/2001 | Olewicz | F16K 31/025 251/11 |
| 6,494,225 B1 * | 12/2002 | Olewicz | F16K 7/045 137/1 |
| 7,093,817 B2 * | 8/2006 | MacGregor | B60H 1/00671 251/11 |
| 7,315,109 B1 | 1/2008 | Griffiths et al. | |
| 7,748,405 B2 * | 7/2010 | Ghorbal | F16K 31/002 137/596.17 |
| 9,562,621 B2 * | 2/2017 | O'Neill | F16K 11/044 |
| 2008/0056920 A1 | 3/2008 | Griffiths et al. | |
| 2010/0021311 A1 | 1/2010 | McNally et al. | |

\* cited by examiner

AUTOMATED NON-MAGNETIC MEDICAL MONITOR USING SHAPE MEMORY ACTUATORS

CROSS REFERENCE TO RELATED APPLICATIONS

This application is a national filing of PCT application Serial No. PCT/IB2013/054828, filed Jun. 13, 2013, published as WO 2013/186725 A2 on Dec. 19, 2013, which claims the benefit of U.S. provisional application Ser. No. 61/658,964 filed Jun. 13, 2012, which is incorporated herein by reference.

The present application finds particular application in magnetic resonance (MR)-compatible patient monitoring devices comprising shape memory alloy (SMA) components. However, it will be appreciated that the described technique may also find application in other patient monitoring devices, other magnetic device systems, or other SMA activation techniques.

Conventional patient monitoring devices such as blood pressure cuffs and the like comprise metal components that are susceptible to magnetic fields (e.g., iron, nickel, cobalt, etc.). Patient monitoring devices comprising such metals can be affected by the large magnets of an MR scanner when the scanner is operational. For instance, a blood pressure cuff valve comprising ferromagnetic components can be affected such that the valve enters a closed state and the cuff acts as a tourniquet on the patient's arm during the MR scan. Moreover, ferromagnetic components of a peripheral device coupled to the patient, such as a pump or the like, which is intended to remain outside the MR scanner during the scan, can be drawn to the magnets of the MR scanner. Depending on the magnitude of the attraction to the magnets, the size and weight of the peripheral device, etc., the peripheral device can cause damage to other equipment in the area, the MR scanner, and/or the patient.

"Ferrous projectiles," as they are known, can cause damage to expensive medical equipment as well as patient injury. In fact, any ferrous material can be detrimental to patient safety. For instance, a patient who is an employee of a steel mill or other similar environment may have microscopic metal shavings in his eye(s) that go undetected before an MR scan. These ferrous projectiles are only detected once the MR scanner magnets have been activated, to the great discomfort of the patient. In the forgoing blood pressure cuff example, the magnetic field generated by the MR scanner magnets can pull a pneumatic valve closed in the cuff. This can result in discomfort to the patient, as well as a deficiency in vital sign information required or desired by a clinician during the MR scan.

Attempts to make MR-safe patient monitoring devices to date have not considered shape memory alloy metals due to the slow actuation period typically required to activate such alloys to achieve a desired response. In the case of patient monitoring devices, slow actuation times are not acceptable where patient vital sign measurements are desired periodically and frequently.

The present application relates to new and improved systems and methods that facilitate rapid activation of shape memory alloy components in MR-compatible patient monitoring devices, which overcome the above-referenced problems and others.

In accordance with one aspect, a valve actuator for actuating a magnetic resonance (MR)-compatible valve, includes a shape memory alloy (SMA) member that when actuated depresses a valve plunger to mate with a valve seat in the MR-compatible valve. The valve actuator further includes a control circuit that provides a power signal to the SMA member to actuate the SMA member and maintain the SMA member in an active state.

In accordance with another aspect, a method of actuating a magnetic resonance (MR)-compatible valve includes providing a constant power signal to a shape memory alloy (SMA) member that when actuated depresses a valve plunger to mate with a valve seat in the MR-compatible valve. The method further includes monitoring at least one valve parameter to detect when the valve is closed, and adjusting the power signal upon detecting that the valve is closed, in order to maintain the SMA member in an active state while reducing power consumption.

In accordance with another aspect, a control circuit that actuates a shape memory alloy (SMA) member to close a magnetic resonance (MR)-compatible valve comprises a driver that provides a constant power signal to the SMA member to actuate the SMA member and cause the SMA member to contract and depress a valve plunger to close the valve, The control circuit further comprises a multiplier that multiplies a measured feedback current by a measured voltage current to generate a feedback power signal that is used to maintain the constant power signal. The control circuit is configured to, in response to an indication that the valve is closed, reduce and pulse width modulate the power signal to conserve power and maintain the SMA member in an active state.

Still further advantages of the subject innovation will be appreciated by those of ordinary skill in the art upon reading and understanding the following detailed description.

The innovation may take form in various components and arrangements of components, and in various steps and arrangements of steps. The drawings are provided for purposes of illustrating various aspects and are not to be construed as limiting the invention.

In magnetic resonance imaging (MRI), powerful magnetic fields can interfere with, damage, cause premature failure in, and attract certain non-MR-safe instruments. The herein described systems and methods mitigate a need for electromagnetically sensitive components in favor of MR-safe shape memory alloy elements. The described valve, for instance, can be positioned near the patient during an MR scan without fear of damage to the valve, danger to the patient or clinician, or the MR machine.

In contrast to conventional valves, MR-safe valves employing shape memory materials are non-magnetic and therefore mitigate a danger of being drawn into the bore of an MR scanner. Their reliability is not affected by strong magnetic fields, and they do not require additional magnetic shielding that may add cost and weight and increases the risk to the patient, clinician and equipment from valve components being drawn towards the magnetic field of the MR machine. MR-compatible valves also mitigate a need for long hoses and cables because the MR-safe equipment may be brought closer to the MR machine and the patient during the MR procedure. Furthermore, the described MR-safe valve provides decreased electrical noise emissions, weight, and power consumption relative to piezoceramic materials. According to one aspect, a control circuit is provided that accelerates actuation of the shape memory material and protects the material from damage caused by power supply variation.

In this manner, the described examples facilitate using a shape memory actuator (e.g., the SMA spring or wire) to close a pneumatic valve. A shape memory element is used to act against the valve spring. The driver circuit quickly, safely and repeatably causes the shape memory actuator to act. The described innovation makes it possible to operate the valve in the MR environment, without risk of damage to the equipment from excessive magnetic fields. It also eliminates danger of the equipment being drawn into the bore and has applications to patient monitoring in the MR environment, and to any form of electromechanical switching, including pneumatic power switching in the MR environment.

Figure 1:
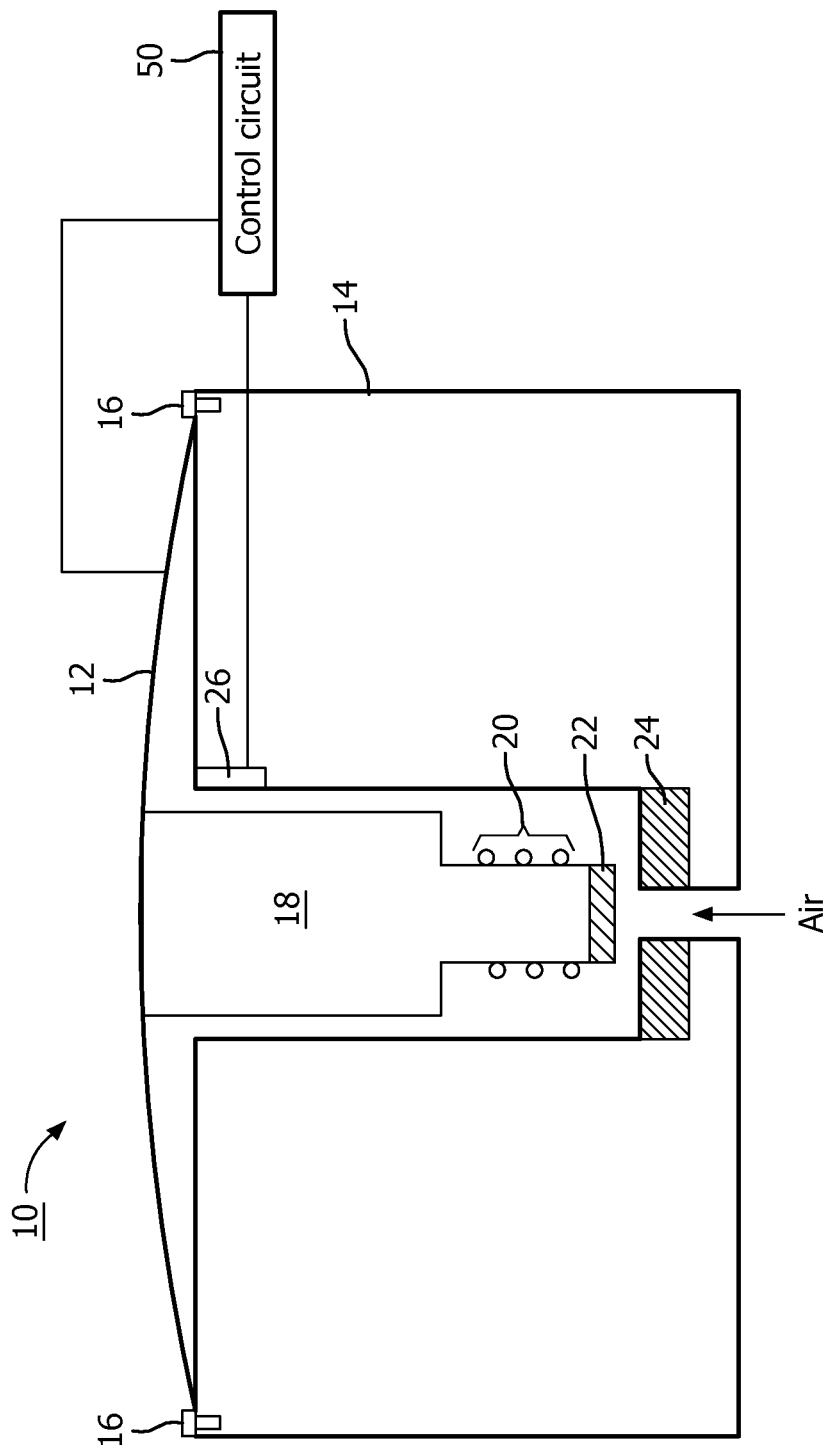
FIG. 1 illustrates a cross-sectional view of a valve with a shape memory alloy (SMA) member (e.g., a spring) that is controlled to open and close an MR-compatible valve that can be employed in the bore of an MR scanner during a scan of a patient, in accordance with various aspects described herein.

FIG. 1 illustrates a cross-sectional view of a valve 10 with a shape memory alloy (SMA) member (e.g., a spring) 12 that is controlled to open and close an MR-compatible value that can be employed in the bore of an MR scanner during a scan of a patient, in accordance with various aspects described herein. For example, the valve may be employed in a blood pressure cuff that monitors a patient's blood pressure during the MR scan. In other embodiments, the valve is employed in other pneumatic or hydraulic valves or plungers (e.g., an intravenous drip regulator or the like) Advantages of shape memory materials over piezoceramic or other MR-compatible solutions include lower cost and less complex drive circuitry. The described valves and/or pumps are capable of operating in a high magnetic field without the use of additional magnetic shielding. Such valves and/or pumps enable the non-invasive monitoring of blood pressure, exhaled gasses and anesthetic gasses in the MRI environment. They may also be used to create MR-compatible electrical switches and valves. The valve assembly 10 of FIG. 1 substitutes non-magnetic materials for conventional magnetic motor and solenoid components in, for example patient monitors and/or peripheral devices for use in the MR environment, while improving performance.

In one embodiment, the SMA member or spring 12 is a nitinol (e.g., nickel titanium) wire, strip, band, etc., which is coupled to a valve body 14 via fasteners 16, although any suitable SMA that exhibits changes in resistance with respect to temperature may be employed. The fasteners may be mechanical, chemical, or any other suitable type of fastener. The resistance of the nitinol wire changes when the wire is heated, and the wire shrinks. The SMA spring overlays a plunger 18 which, when depressed via the contraction of the wire, closes the valve. In one embodiment, an over-pressure spring (not shown) is provided between the SMA spring 12 and a top surface of the plunger 18.

A valve spring 20, shown in cross-section as a plurality of dots on either side of the plunger stem, biases the plunger upward to maintain the valve in an open state until the SMA spring is activated. In the vase where the valve 10 is a pneumatic valve, the valve spring 20 may be optional. When activated, the SMA spring forces the plunger downward to close the valve and stop the flow of air (or some other gas or liquid) by forcing the plunger tip 22 against a valve seat 24. A sensor 26 (e.g., a position sensor, a pressure sensor, or any other suitable sensor) is also included for determining whether the valve is open or closed. Once the sensor indicates to a control circuit 50 that the valve is closed, power supplied by the control circuit to the SMA spring switches from a constant power level (e.g., 3 W or some other suitable power level) to a pulse width modulated power level (e.g., pulses with power levels between approximately 0 W and 3 W or the like) to reduce power consumption and prevent damage to the spring. In another embodiment, the constant power level is maintained for the duration of the operation of the valve and/or device in which the valve is employed.

A shape-memory alloy also known as SMA, smart metal, memory metal, memory alloy, muscle wire, smart alloy) is an alloy that remembers its original, cold-forged shape that returns to a pre-deformed shape by heating. The heat may be applied by external source or by passing a current through the material. Shape memory alloys include, but are not limited to copper-zinc-aluminum-nickel, copper-aluminum-nickel, beryllium-copper, copper bronze, and nickel-titanium. The activation of a memory shape alloy element is dependent on the temperature of the element and involves a change in state of the element material. The resistivity of the element changes with state change of the element.

Figure 2:
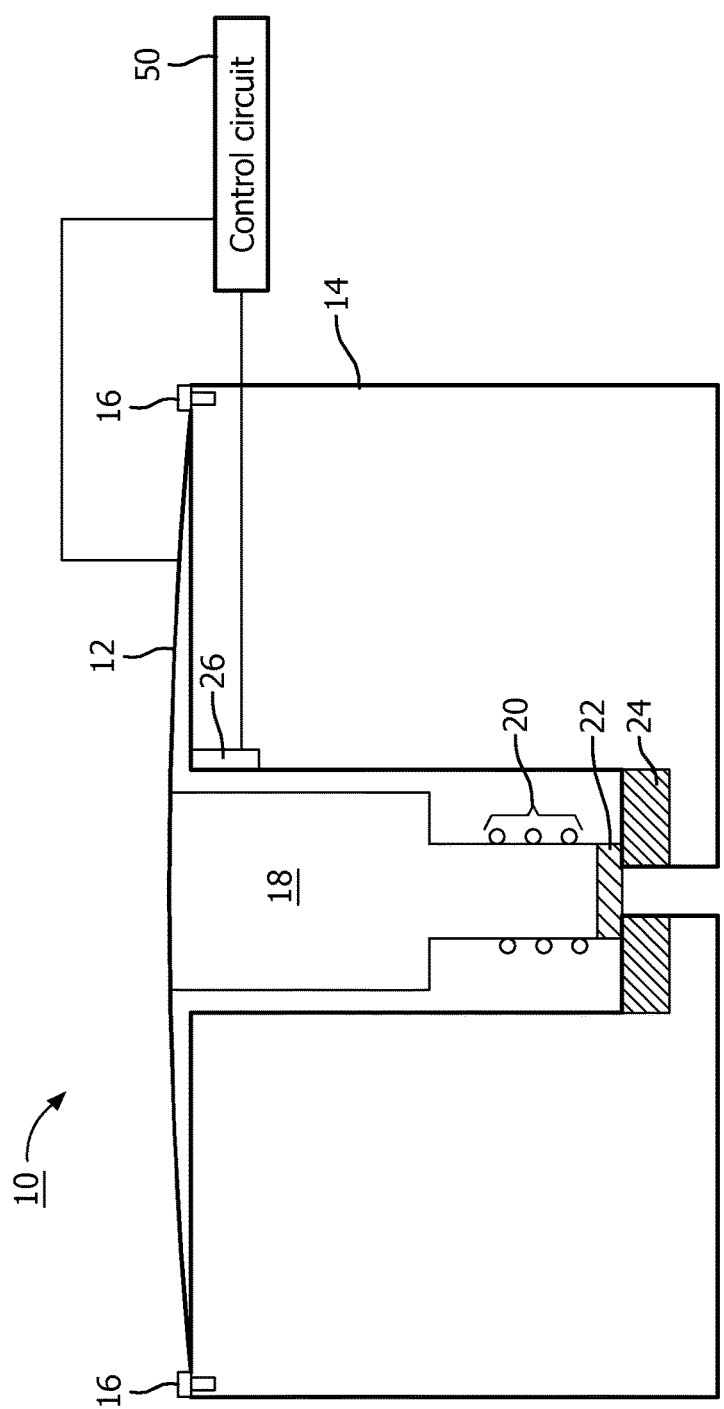
FIG. 2 illustrates a cross-sectional view of a valve in the closed position (e.g., after actuation of the SMA spring), in accordance with various aspects described herein.

FIG. 2 illustrates a cross-sectional view of a valve 10 in the closed position (e.g., after actuation of the SMA spring), in accordance with various aspects described herein. The valve includes the SMA spring 12, which is coupled to a valve body 14 via fasteners 16. The actuated SMA spring biases the plunger 18 downward to maintain the valve in a closed state. The valve spring 20 biases the plunger upward to maintain the valve in an open state when the SMA spring is not activated. When activated, the SMA spring forces the plunger downward to close the valve and stop the flow of air (or some other gas or liquid) by forcing the plunger tip 22 against the valve seat 24. The sensor 26 is also included for determining whether the valve is open or closed.

Figure 3:
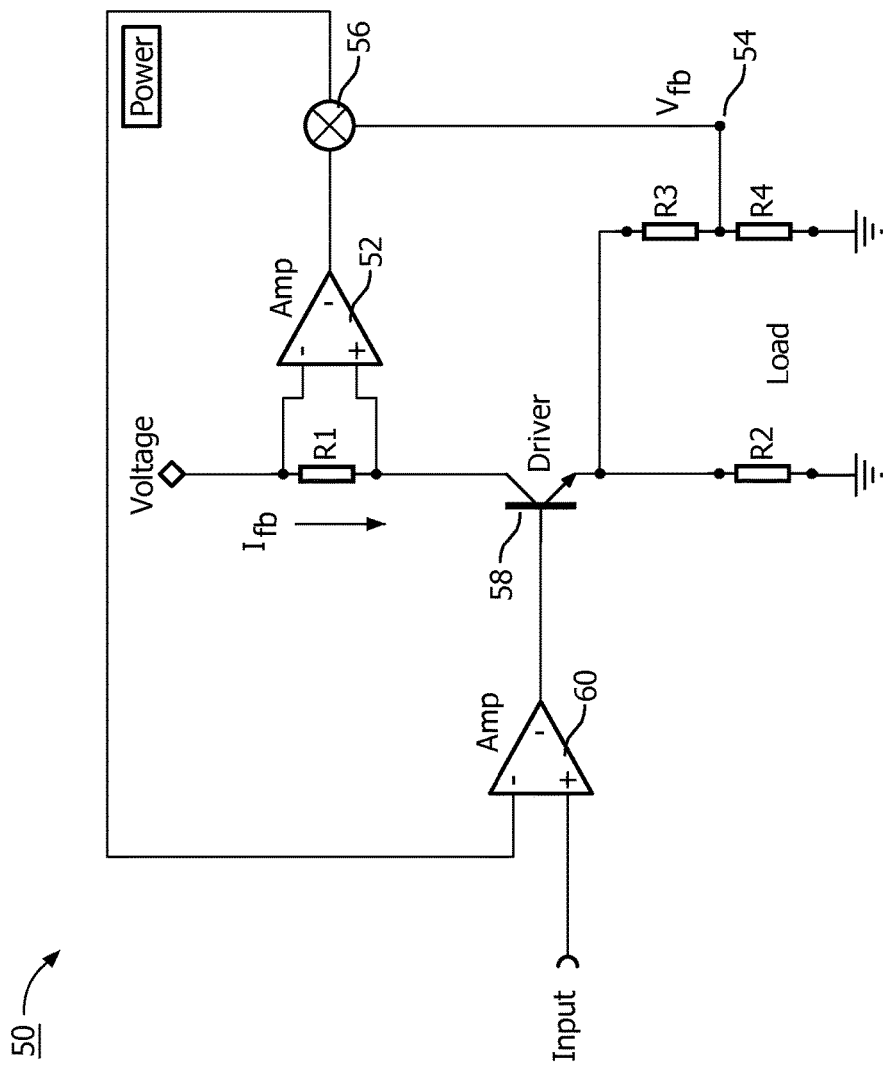
FIG. 3 illustrates a control circuit that actuates the SMA spring (FIGS. 1 and 2) and protects it from power surges and/or other damaging events, in accordance with various aspects described herein.

FIG. 3 illustrates a control circuit 50 that actuates the SMA spring (FIGS. 1 and 2) and protects it from power surges and/or other damaging events, in accordance with various aspects described herein. The circuit comprises a high side current monitor comprising amplifier 52 to monitor the load current, a load voltage feedback point 54, a multiplier 56 to multiply the load current and load voltage, a pass element 58 that delivers current and voltage to the load R2 (e.g., the SMA wire 12), and an error amplifier 60 and pass element driver R1.

The circuit also comprises a voltage divider comprising resistors R3 and R4, as illustrated. The multiplier 56 evaluates current (I) and voltage (V) delivered to the load (e.g., the nitinol wire) and provides feedback signal that controls an input voltage the error amplifier 60. The voltage divider generates voltage feedback signal, while the current across R1 provides current feedback signal. The feedback signals are multiplied 56 and provided to the error amplifier 60 allowing constant power to be delivered to the load. In contrast to conventional SMA actuation approaches, which only control one of voltage or current, the described circuit 50 controls both current and voltage, and via the multiplier 56, controls power to provide a constant power level. Once the SMA spring is contracted and the plunger is depressed to close the valve, the constant power level is maintained, or alternatively is reduced and pulse width modulation is applied to conserve power. The circuit response is tuned to allow control even when the control input is pulse width modulated to conserve power during activation state hold times. The described circuit energizes the SMA spring using a feedback of applied current times applied voltage, yielding applied power feedback. This feature allows consistent and fast activation by applying the maximum activation power in all activation and transition states.

When the SMA spring 12 is heated, resistance increases such that voltage across the spring increases and current through the spring decreases. In this event, the multiplier provides constant power to the SMA spring, but within an acceptable limit to avoid damage to the SMA spring. In one embodiment, the multiplier provides approximately 3 W of power at approximately a 1V control input for a predetermined time period, and then the supplied power control signal is pulse width modulated between 0V and 1V to maintain the spring in a heated and contracted state while managing power consumption. In another embodiment, the multiplier provides approximately 3 W of power at approximately a 1V control signal for a desired time period after which the valve is permitted to open. In any event, power through the load is limited to prevent burning and/or excessive contraction of the SMA spring.

Figure 4:
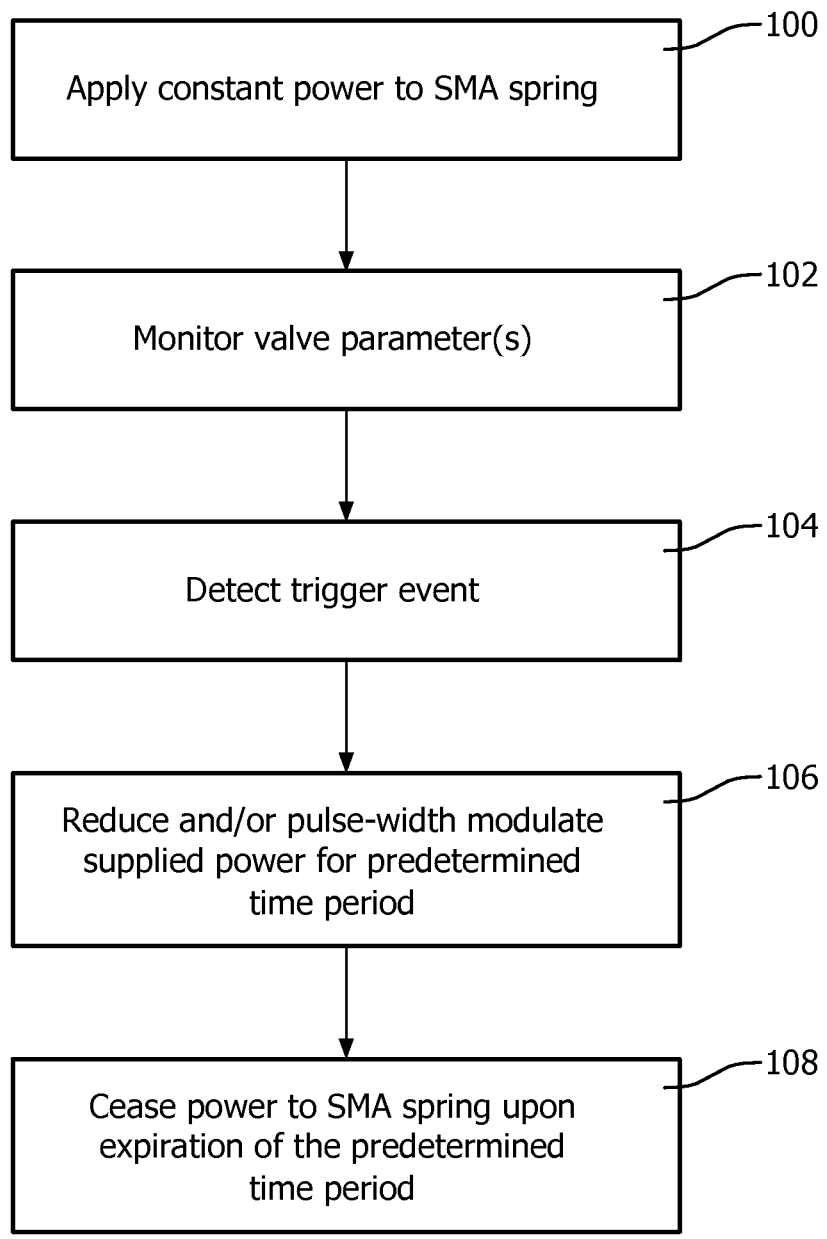
FIG. 4 illustrates a method of controlling an SMA spring in an MR-compatible valve assembly that can be employed in a pump, a blood pressure cuff, or any other device that is positioned in or near a bore of an MR scanner, in accordance with various aspects described herein.

FIG. 4 illustrates a method of controlling an SMA spring in an MR-compatible valve assembly that can be employed in a pump, a blood pressure cuff, or any other device that is positioned in or near a bore of an MR scanner, in accordance with various aspects described herein. At 100, a constant power level is supplied to the SMA spring. In one example, the power level is in the range of approximately 2-5 W. In another example, the power level is approximately 3 W. At 102, one or more valve parameters are monitored. For instance, a pressure in the valve or in a blood pressure cuff in which the valve is employed can be monitored. In another example, plunger position is monitored to facilitate determining whether the valve is in an open state or a closed state.

At 104, a trigger event is detected. For instance, once the pressure is determined to have exceeded a predetermined pressure threshold, the valve is determined to be closed. In another example, the determination that the position of the plunger is indicative of a closed valve is used as a trigger event. At 106, upon detection of the trigger event, the constant power supplied to the SMA spring to actuate it is reduced and pulse width modulated (e.g., pulses with power levels between approximately 0 W and 3 W, or some other suitable reduced power level) to control power consumption while maintaining the SMA spring in its active state (e.g., contracted in the described example). In one embodiment, a predetermined time period (e.g., on the order of milliseconds, seconds, etc.) is counted down between detection of the trigger event and adjustment of the supplied power. At 108, upon expiration of a predetermined operational time period, power to the SMA spring is ceased. For example, the predetermined operational time period may be approximately 40 seconds in order to permit the patient's blood pressure to be measured. In any event, the operational time period represents an approximate amount of time that the valve remains closed to perform its function in the device in which it is employed.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

The invention claimed is:

1. A valve actuator for actuating a valve, the valve actuator including:
    a shape memory alloy (SMA) member that when actuated depresses a valve plunger to mate with a valve seat in the valve;
    a control circuit that provides a power signal having a constant power level to the SMA member to actuate the SMA member and maintain the SMA member in an active state; and
    a position sensor that detects when the plunger is in a closed position, and indicates to the control circuit that the valve is closed;
    wherein the control circuit reduces and pulse width modulates the power signal between 0 W and the constant power level used to actuate the SMA member in response to the indication that the valve is closed, thereby maintaining the SMA member in the active state at a reduced PWM power level and keeping the valve closed for a predetermined time period.

2. The valve actuator according to claim 1, wherein the SMA member is a nitinol wire that contracts and biases the plunger downward when actuated.

3. The valve actuator according to claim 2, wherein the control circuit supplies a constant power to the nitinol wire to actuate the nitinol wire.

4. The valve actuator according to claim 1, wherein the sensor is a pressure sensor that determines that the valve is in a closed state when pressure in the valve exceeds a predetermined pressure threshold.

5. The valve actuator according to claim 1, wherein the control circuit measures a current feedback signal and a voltage feedback signal and includes a multiplier that multiplies the current feedback signal and the voltage feedback signal to generate a power feedback signal that is employed to provide a constant power signal to the SMA member during actuation.

6. The valve actuator according to claim 1, wherein the SMA member comprises at least one of:
    copper-zinc-aluminum-nickel;
    copper-aluminum-nickel;
    beryllium-copper;
    copper bronze; and
    nickel-titanium.

7. The valve actuator according to claim 1, further comprising a valve spring that biases the plunger upward against the SMA member.

8. The valve actuator according to claim 1, employed in an MR-compatible blood pressure monitoring system.

9. A method of actuating a valve, the method including:
    providing a constant power signal having a constant power level to a shape memory alloy (SMA) member that when actuated depresses a valve plunger to mate with a valve seat in the valve;
    monitoring at least one valve parameter to detect when the valve is closed;
    adjusting the power signal upon detecting that the valve is closed, in order to maintain the SMA member in an active state while reducing power consumption;
    wherein the at least one monitored parameter is plunger position; and
    wherein adjusting the power signal comprises reducing and pulse width modulating the power signal between 0 W and the constant power level used to actuate the SMA member in response to an indication that the valve is closed, thereby maintaining the SMA member in the active state at the reduced PWM power level and keeping the valve closed for a predetermined time period.

10. The method according to claim 9, wherein the SMA member is a nitinol wire that contracts and biases the plunger downward when actuated.

11. The method according to claim 9, wherein the at least one monitored parameter is pressure in the valve, and further comprising determining that the valve is closed upon detecting that the monitored pressure has exceeded a predetermined pressure threshold.

12. The method according to claim 9, wherein providing a constant power signal comprises:
measuring a current feedback signal and a voltage feedback signal;
multiplying the current feedback signal by the voltage feedback signal to generate a power feedback signal; and
employing the power feedback signal to generate the constant power signal to the SMA member during actuation.

13. The method according to claim 9, wherein the SMA member comprises at least one of:
copper-zinc-aluminum-nickel;
copper-aluminum-nickel;
beryllium-copper;
copper bronze; and
nickel-titanium.

14. A control circuit that actuates a shape memory alloy (SMA) member to close a magnetic resonance (MR)-compatible, non-magnetic valve, the control circuit comprising:
a driver that provides a constant power signal having a constant power level to the SMA member to actuate the SMA member and cause the SMA member to contract and depress a valve plunger to close the valve; and
a multiplier that multiplies a measured feedback current by a measured voltage current to generate a feedback power signal that is used to maintain the constant power signal;
wherein the control circuit is configured to receive from a position sensor an indication that that the valve is closed based at least in part on a detected plunger position;
wherein the control circuit is configured to, in response to an indication that the valve is closed, reduce and pulse width modulate the power signal between 0 W and the constant power level used to actuate the SMA member to conserve power and maintain the SMA member in an active state thereby keeping the valve closed for a predetermined time period.

15. The control circuit according to claim 14, wherein the SMA member is a nitinol wire that biases a valve plunger downward when actuated to close the valve and maintain the valve in a closed state until the power signal is terminated.

* * * * *